United States Patent [19]

Forde

[11] Plant 4,389

[45] Feb. 27, 1979

[54] WALNUT TREE

[75] Inventor: Harold I. Forde, Davis, Calif.

[73] Assignee: The Regents of the University of California, Berkeley, Calif.

[21] Appl. No.: 898,598

[22] Filed: Apr. 21, 1978

[51] Int. Cl.[2] ..... A01H 5/03

[52] U.S. Cl. ..... Plt./32

[58] Field of Search ..... Plt./32

*Primary Examiner*—Robert E. Bagwill
*Assistant Examiner*—James R. Feyrer

[57] ABSTRACT

A new and distinct, very productive tree which produces walnuts which are nearly elliptical in shape; being round in cross section. The kernel averages about 59 percent.

2 Drawing Figures

This invention relates to a new and distinct cultivar of walnut tree, botanical classification *Juglans regia.* The original tree grew from a seed from the University of California Walnut Breeding Program, in 1966.

A continuous walnut breeding program has been maintained by the University of California from 1948 to the present. In 1965, pistillate flowers of the cultivar Lompoc were bagged and pollinated with pollen from Pl 159568. This selection, U.C. 66-4, grew from one of the resulting seeds, therefore, the parents of this selection are Lompoc and Pl 159568. Lompoc, had been released as a cultivar from the University of California Walnut Breeding Program by E. F. Serr and Harold I. Forde in 1968. Lompoc resulted from crossing Waterloo × Payne in 1951. Pl 159568 had been brought into this country from Afghanistan, by the U.S. Bureau of Plant Introduction.

Thirty-one seedlings of the cross Lompoc × Pl 159568 were established in the test orchard on the campus of the University of California, Davis. The resulting seedlings were maintained under careful and continuous observation. When such seedlings bore fruit, one (the instant cultivar) evidenced novel and commercially desirable characteristics and was selected for asexual reproduction to permit further testing and possible introduction to the trade.

After its origin, as above, the cultivar named "Sunland" was asexually reproduced by top grafting on trees of the two common rootstocks, Northern California black walnut, *Juglans hindsii,* and Paradox, *J. hindsii* × *J. regia,* in the University of California (Department of Pomology) experimental orchard. Subsequently, it was also asexually propagated by grafting in test plots in some of the walnut growing areas of California. The tests evidenced that the trees, leaves, buds, and fruit resulting from such reproductions all ran true to the parent trees in every respect.

Figure 1:
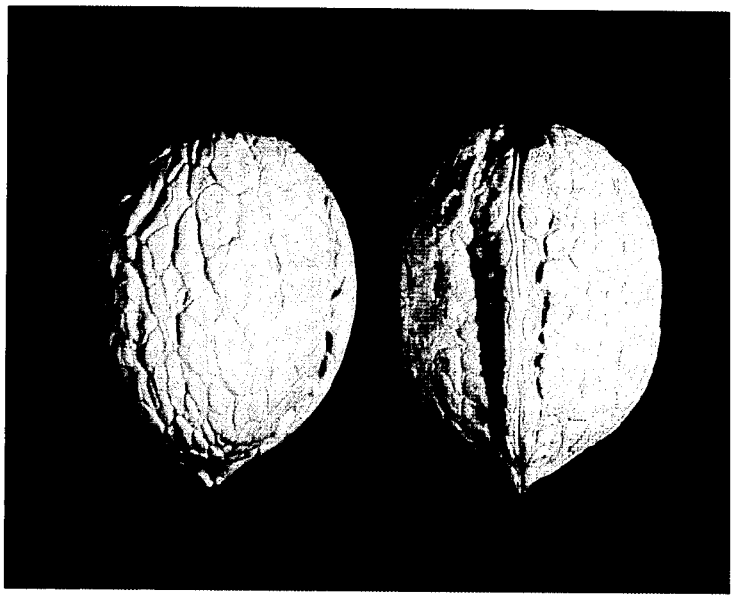
FIG. 1 illustrates a nut in the shell, typical of the new variety.
Figure 2:
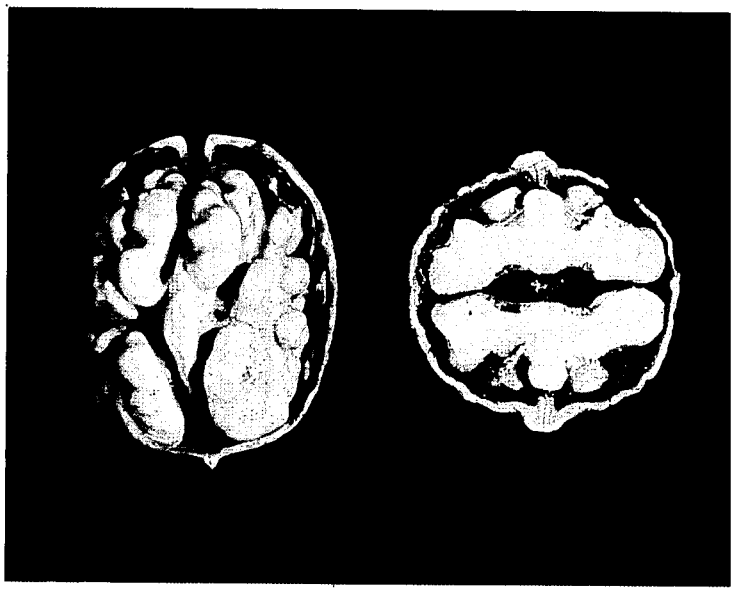
FIG. 2 illustrates the nut in cross section and also a longitudinal view of the nut with half the shell removed.
Figure 3:
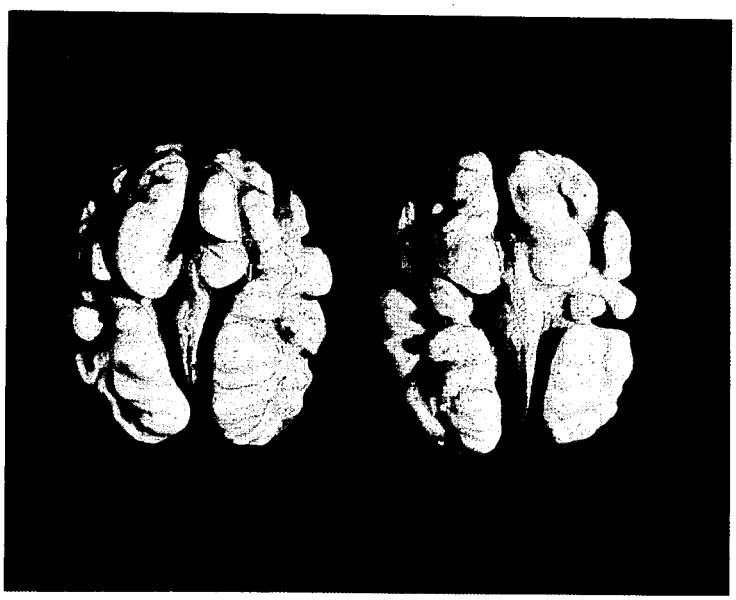
FIG. 3 illustrates kernel halves of the nut of the new variety.

This new and distinct variety of walnut tree produces high percent kernel which varies from 56 to 61 percent with an average of about 59 percent. The nut shell is thin and very well filled and sealed, having plump kernels of good quality. Primary use of the fruit of this variety would be for shelling and sale as kernels. As will be seen from the botanical description, the nut has good shell color, bleach ability, good shell seal, and smoothness of shell, thereby also making this cultivar suitable for sale of nuts in the shell.

It is understood that the tree and fruit of the new cultivar may vary in slight detail due to climatic and soil conditions under which it is grown but without loss of its distinguishing characteristics.

The new and distinct cultivar of walnut is characterized by its spreading growth, moderate vigor and early and heavy production. Nearly all shoots from terminal buds and about 80 percent of the shoots from the axillary buds produce pistillate flowers. The time when growth commences is about the same as the start of growth for Payne and the nuts are ready for harvesting about two or three days after Hartley.

Of the walnut cultivars now in use, only Lompoc commences growth as early as the present variety, is ready to harvest as late and has as many flowers on shoots from axillary buds. However, Lompoc, the female parent of this selection, differs greatly from the present variety in respect to nut shape and quality. The nut of the present variety is elliptical in longitudinal section and round in cross section. The apex of the nut has a small beak-shaped point and the shell is thin, light colored, smooth and very well sealed. In well-grown lots of nuts most of the kernels are light colored with some light amber and amber. As stated, kernel percent has averaged about 59 percent.

The botanical details of this new and distinct cultivar are as follows:

*Tree.*—Size, medium (similar to Ashley or Payne); vigor, moderately vigorous; growth, somewhat spreading tree, tending to be as wide as it is tall and with a round top; production, very productive; bearing, early regular bearer.

*Trunk and branches.*—Like most other *J. regia.* Old bark light gray and smooth, very old bark probably roughens as it does in other walnuts. New shoots have green bark which turns brown as the season progresses, like other walnuts.

*Leaves.*—Leaves are pinnately compound with 5 to 9 leaflets per leaf. Leaves are green with lower surface being lighter green than the top.

Leaves vary in length from about 25 to 48 cm., averaging about 38 cm. Leaflets vary in length from about 5 to 19 cm., averaging about 15 cm. and in width from about 3 to 11 cm., averaging about 8 cm. The basal leaflets are smaller with the terminal leaflet and the leaflets next to it being the largest.

Leaflet shape is elongated ovate to nearly elliptical. Leaflets have acute apices and bases of leaflets are mostly rounded with some uneven. Uneven bases have the blade on one side of the mid-rib 2 to 5 mm. farther from the rachis than it is on the other side. Leaf texture, smooth; margin, smooth; and venation, pinnate.

Start of growth and leafing dates are early, having been zero to five days after Payne, averaging about one or two days after Payne.

*Inflorescence.*—The cultivar is very precocious, young grafted trees having produced pistillate flowers at two years of age and catkins at three. About 80 percent of the axillary (lateral) buds produce pistillate flowers.

Full bloom of pistillate flowers has been 25 to 38 days after leafing date of Payne, averaging 32 days. First pollen shedding has been six to 18 days after leafing date of Payne with the average being 11 days. Last pollen shedding has been 23 to 28 days after Payne leafing with an average of 25 days. Calendar dates in 1976 were pistillate full bloom, April 18; first pollen shed March 22; and last pollen shed April 14. The trees have produced many catkins. Most flowering tips have two pistillate flowers, some have three, a few have one and a few have more than three. There is nothing distinctive about the form or color of the male or female flowers as they are similar to most other walnut flowers.

*The fruit.*—The green fruit before it is ready to harvest is elliptical in longitudinal section and round in cross section. The hull is green with small lenticels and is of about average thickness, the hull is similar in appearance and thickness to the hull of the Payne variety.

*The nut.*—The shape of the nut in longitudinal section is elliptical with a small beak-shaped point at the apical end, the cross section is round. An average well-grown nut would have a length of about 45 mm., a suture diameter of about 35 mm. and a cheek diameter of about 35 mm.

The nut shell is medium light colored and is quite smooth, having small longitudinal grooves and some small pits.

The kernel color refers to standard U.S. Department of Agriculture grading chart.

The nut shell is thin, very well filled and well sealed. The kernel is plump. In 1976, a 500 gr. random sample from the plot at Davis contained 29 nuts and, based on total in-shell weight, had 47 percent light, 6 percent light amber, 7 percent amber and no off-grade for a total of 60 percent kernel. Percent light in other samples has varied from about 36 percent to 58 percent, with an average of about 48 percent. Percent kernel has varied from about 56 to 61 percent with an average of about 59 percent.

*Harvest.*—Nuts of this cultivar are ready to harvest about 16 days after Payne which is about two or three days later than Hartley and about the same time as Lompoc.

I claim:

1. The new and distinct cultivar of walnut tree herein described and illustrated and characterized by its spreading growth, moderate vigor, heavy production and mid-season harvest; said variety having its start of growth and leafing about the same time as Payne and a harvest time about the same as Lompoc, namely about two or three days after Hartley and 16 days after Payne; said variety being further characterized by the production of pistillate flowers on nearly all shoots from terminal buds and on about 80 percent of shoots from axillary buds; said variety being primarily characterized by its nut the kernel of which is light in color with some light amber and amber; said nut being elliptical in longitudinal section, round in cross section and having a nut apex which terminates in a small beak-shaped point; said variety also being characterized by its nut shell, which is thin, light colored, smooth and well filled and sealed.

* * * * *